United States Patent
Phan et al.

(10) Patent No.: US 10,617,154 B2
(45) Date of Patent: Apr. 14, 2020

(54) SINTERED BODY WITH ELECTRICALLY CONDUCTIVE COATING

(71) Applicant: SCHOTT AG, Mainz (DE)

(72) Inventors: Dang Cuong Phan, Aachen (DE); Julia Gold, Buchbach (DE); Matthias Rindt, Landshut (DE); Susanne Schmid, Rottenburg (DE); Thomas Beerhorst, Ältfranzhofen (DE)

(73) Assignee: SCHOTT AG, Mainz (DE)

( * ) Notice: Subject to any disclaimer, the term of this patent is extended or adjusted under 35 U.S.C. 154(b) by 0 days.

(21) Appl. No.: 16/151,840

(22) Filed: Oct. 4, 2018

(65) Prior Publication Data
US 2019/0098935 A1    Apr. 4, 2019

(30) Foreign Application Priority Data
Oct. 4, 2017  (DE) .................. 10 2017 123 000

(51) Int. Cl.
*A24F 47/00*    (2020.01)
*F24F 6/00*    (2006.01)
(Continued)

(52) U.S. Cl.
CPC ......... *A24F 47/008* (2013.01); *A01M 1/2022* (2013.01); *A61L 9/037* (2013.01);
(Continued)

(58) Field of Classification Search
None
See application file for complete search history.

(56) References Cited

U.S. PATENT DOCUMENTS 2,741,508 A  * 4/1956  Marantz ............... B05B 7/168
                                                    239/597
2,966,430 A  * 12/1960 Schrewelius ........... H01B 1/00
                                                    313/342
(Continued)

FOREIGN PATENT DOCUMENTS

CN       105725281 A     7/2016
DE       1288705         2/1969
(Continued)

OTHER PUBLICATIONS

German Office Action dated May 23, 2018 with translation from corresponding German Application No. 10 2017 123 000.9.
(Continued)

*Primary Examiner* — Thor S Campbell
(74) *Attorney, Agent, or Firm* — Ohlandt, Greeley, Ruggiero & Perle, L.L.P.

(57) ABSTRACT

A porous sintered body with an electrically conductive coating is provided. The sintered body has an open porosity in a range from 10 to 90%. The electrically conductive coating is bonded to the surface of the pores and is part of a heating device in a vaporizer. The electrically conductive coating lines the pores located in the interior of the sintered body so that when the sintered body is electrically connected and a current is applied, the current flows at least partially through the interior of the sintered body so that the interior of the sintered body is heated. A method for producing a porous sintered body with an electrically conductive coating is also provided.

33 Claims, 4 Drawing Sheets
(3 of 4 Drawing Sheet(s) Filed in Color)

(51) Int. Cl.
| | |
|---|---|
| *C03C 17/10* | (2006.01) |
| *C03C 4/02* | (2006.01) |
| *C03B 19/08* | (2006.01) |
| *C03C 11/00* | (2006.01) |
| *A01M 1/20* | (2006.01) |
| *C03B 19/06* | (2006.01) |
| *C03C 17/36* | (2006.01) |
| *C03C 3/093* | (2006.01) |
| *A61M 11/04* | (2006.01) |
| *A61L 9/03* | (2006.01) |
| *C03C 3/087* | (2006.01) |
| *C03C 3/091* | (2006.01) |
| *C03C 3/095* | (2006.01) |
| *C03C 3/097* | (2006.01) |
| *C03C 3/11* | (2006.01) |
| *C03C 10/00* | (2006.01) |
| *C03C 17/25* | (2006.01) |

(52) U.S. Cl.
CPC ......... *A61M 11/042* (2014.02); *C03B 19/06* (2013.01); *C03B 19/08* (2013.01); *C03C 3/087* (2013.01); *C03C 3/091* (2013.01); *C03C 3/093* (2013.01); *C03C 3/095* (2013.01); *C03C 3/097* (2013.01); *C03C 3/11* (2013.01); *C03C 4/02* (2013.01); *C03C 10/0018* (2013.01); *C03C 11/00* (2013.01); *C03C 17/10* (2013.01); *C03C 17/25* (2013.01); *C03C 17/3607* (2013.01); *F24F 6/00* (2013.01); *A61L 2209/135* (2013.01); *A61M 2205/0205* (2013.01); *A61M 2205/0211* (2013.01); *A61M 2205/0233* (2013.01); *A61M 2205/0238* (2013.01); *A61M 2205/36* (2013.01); *A61M 2205/3673* (2013.01); *A61M 2205/8206* (2013.01); *C03C 2217/23* (2013.01); *C03C 2217/231* (2013.01); *C03C 2217/241* (2013.01); *C03C 2217/244* (2013.01); *C03C 2217/70* (2013.01); *C03C 2218/111* (2013.01); *C03C 2218/32* (2013.01)

(56) References Cited

U.S. PATENT DOCUMENTS

| | | | | |
|---|---|---|---|---|
| 3,477,827 | A | * | 11/1969 | Mott .................. B01J 15/005 392/473 |
| 3,688,083 | A | * | 8/1972 | Rice .................. F22B 1/28 392/488 |
| 4,347,429 | A | * | 8/1982 | Will .................. F22B 1/30 204/291 |
| 5,073,625 | A | * | 12/1991 | Derbyshire ............ B01D 35/18 210/184 |
| 5,117,482 | A | * | 5/1992 | Hauber ................ H05B 3/148 239/135 |
| 5,146,536 | A | * | 9/1992 | Westover .............. H01C 7/022 219/505 |
| 5,573,984 | A | | 11/1996 | Breitenbuecher |
| 5,633,081 | A | | 5/1997 | Clough |
| 7,317,871 | B2 | * | 1/2008 | Tennison .............. H05B 3/145 392/465 |
| 2003/0108744 | A1 | | 6/2003 | Kuchler |
| 2008/0102310 | A1 | | 5/2008 | Thompson |
| 2011/0226236 | A1 | | 9/2011 | Buchberger |
| 2013/0104916 | A1 | * | 5/2013 | Bellinger ............ A61M 11/041 131/328 |
| 2014/0060554 | A1 | * | 3/2014 | Collett ............... H05B 3/265 131/328 |
| 2014/0238422 | A1 | | 8/2014 | Plunkett |
| 2014/0238423 | A1 | | 8/2014 | Tucker |
| 2014/0238424 | A1 | | 8/2014 | Macko |
| 2015/0090281 | A1 | | 4/2015 | Chen |
| 2017/0042242 | A1 | | 2/2017 | Hon |
| 2017/0105455 | A1 | | 4/2017 | Qiu |
| 2018/0162769 | A1 | | 6/2018 | Peuchert |

FOREIGN PATENT DOCUMENTS

| | | |
|---|---|---|
| DE | 4417739 | 6/1995 |
| EP | 2764783 | 8/2014 |
| GB | 1096375 | 12/1967 |
| JP | 2015015261 | 1/2015 |
| WO | 2017025383 | 2/2017 |

OTHER PUBLICATIONS

DIN 66 133, "Determination of pore volume distribution and specific surface area of solids by mercury intrusion", Jun. 1993, with English translation, 6 pages.

DIN EN ISO 1183-1, "Methods for determining the density of non-cellular plastics—Part 1: Immersion method, liquid pyknometer method and titration method", Apr. 2013, 15 pages.

Bartholomew, "Preparation of Thick Crystalline Films of Tin Oxide and Porous Glass Partially Filled with Tin Oxide", Research and Development Laboratories Corning Glass Works, Corning, New York, Journal of the Electrochemical Society, 1969, pp. 1205-1208.

United Kingdom Office Action dated Dec. 20, 2018 from corresponding UK Application No. GB1816152.1, 6 pages.

* cited by examiner

SINTERED BODY WITH ELECTRICALLY CONDUCTIVE COATING

CROSS REFERENCE TO RELATED APPLICATIONS

This application claims benefit under 35 U.S.C. 119 of German Patent Application No. 10 2017123 000.9 filed Oct. 4, 2017, the entire contents of which are incorporated herein by reference.

BACKGROUND

1. Field of the Invention

The invention generally relates to a sintered body coated with an electrically conductive coating. More particularly, the invention relates to a vaporizer unit comprising a liquid reservoir and a heating unit for storage and controlled release of vaporizable substances. The vaporizer unit can be used in particular in electronic cigarettes, in medication administration devices, room humidifiers, and/or heatable vaporizers for the release of substances into room air, such as fragrances or insect repellents, for example.

2. Description of Related Art

Electronic cigarettes, also referred to as e-cigarettes below, are increasingly being used as an alternative to tobacco cigarettes. Typically, electronic cigarettes include a mouthpiece and a vaporizer unit and an electrical power source operatively connected to the vaporizer unit. The vaporizer unit includes a liquid reservoir which is connected to a heating element.

Certain medications, especially medications for treating the respiratory tract and/or oral and/or nasal mucosa are beneficially administered in the vaporized form, e.g. as an aerosol. The vaporizers of the invention can be used for the storage and administration of such medication, in particular in administration devices for such medication.

Thermally heated vaporizers are increasingly used to provide an ambience with fragrant substances, in particular in bars, hotel lobbies, and/or vehicle interiors, such as the interiors of motor vehicles, in particular automobiles. The vaporizer unit used in this case also has a liquid reservoir connected to a heating element. The liquid reservoir contains a liquid which is usually a carrier liquid, such as propylene glycol or glycerol, in which additives are dissolved and/or, more generally, contained, such as fragrant and flavoring substances, and/or nicotine, and/or medications. The carrier liquid is bonded to the inner surface of the liquid reservoir by adsorption processes. Optionally, a separate liquid reservoir is provided to supply liquid to the liquid reservoir.

Generally, the liquid stored in the liquid reservoir is vaporized by heating the/a heating element, desorbed from the wetted surface area of the liquid reservoir, and can be inhaled by the user. Here, temperatures of over 200° C. may temporarily be reached.

The liquid reservoir therefore has to exhibit high uptake capability and a high adsorption effect, however, at the same time the liquid has to be released rapidly at high temperatures.

From the prior art, different materials are known for use as a liquid reservoir. For example, the liquid reservoir can be defined by a porous or fibrous organic polymer. Although such liquid reservoirs are manufactured quite easily, there is a risk in this case that the polymer material might become too hot and decompose, for example when the liquid reservoir runs dry. This would not only adversely affect the service life of the liquid reservoir or the vaporizer unit, moreover there is the risk that decomposition products of the fluid to be vaporized or even of the liquid reservoir are released and inhaled by the user.

Electronic cigarettes which have porous liquid reservoirs made of organic polymers are known from the prior art. Due to the low temperature stability of the polymeric material, it is therefore necessary to keep a minimum spacing between the heating element and the liquid reservoir, which prevents a compact design of the vaporizer unit and hence of the electronic cigarette. As an alternative to keeping a minimum spacing, a wick can be used that leads the liquid to be vaporized to the heating coil, by capillary forces. This wick is usually made of glass fibers. Although these glass fibers exhibit high temperature stability, the individual glass fibers tend to break easily, however. The same applies if the liquid reservoir itself is made of glass fibers. Therefore, there is a risk that the user inhales loosened or partially dissolved fiber fragments. As an alternative, wicks made of cellulose fibers, cotton or bamboo fibers can be used. Although the risk of breakage is lower with such wicks than with wicks made of glass fibers, they exhibit lower heat stability.

Therefore, vaporizer units with a liquid reservoir made of porous glasses or ceramics are becoming increasingly used. The higher temperature stability of such liquid reservoirs allows to realize a more compact design of the vaporizer and thus of the electronic cigarette as a whole.

Local vaporization can be achieved in practice by a low pressure associated with a high temperature. In an electronic cigarette, the low pressure is realized, for example, by the suction pressure when drawing on the cigarette during consumption, so it is the consumer who regulates the pressure. The temperatures required in the liquid reservoir for vaporization are produced by a heating unit. Usually, a temperatures of more than 200° C. is reached here, in order to ensure rapid vaporization.

The heating power is mostly provided by an electric heating coil powered by a disposable or rechargeable battery. The required heating power depends on the volume to be vaporized and the efficiency of heating. In order to avoid decomposition of the liquid due to excessive temperatures, the heat transfer from the heating coil to the liquid should occur through contactless radiation. For this purpose, the heating coil is mounted as close as possible to the vaporization surface, but preferably without touching it. If, however, the coil touches the surface, the liquid is often overheated and decomposed.

Overheating of the surface may, however, also occur during heat transfer by contactless radiation. The overheating usually occurs locally on the surface of the vaporizer facing the heating coil.

This is the case when a large amount of vapor is needed in operation and the liquid transport to the surface of the vaporizer does not occur fast enough. In this case, the energy supply from the heating element cannot be consumed for vaporization, the surface dries out and may locally heat up to temperatures well above the vaporization temperature, and/or the temperature stability of the liquid reservoir is exceeded. Accurate temperature adjustment and/or control is therefore essential. However, a drawback hereof is the resulting complex structure of the electronic cigarette, which manifests itself in high production costs, among others. In addition, vapor generation is possibly reduced due to the temperature control, and so the maximum possible steam intensity.

EP 2 764 783 A1 describes an electronic cigarette with a vaporizer which has a porous liquid reservoir made of a sintered material. The heating element may be formed as a heating coil or as an electrically conductive coating, the coating being deposited only on portions of the lateral surfaces of the liquid reservoir. Thus, vaporization again occurs in locally limited manner here.

US 2011/0226236 A1 discloses an inhaler in which the liquid reservoir and the heating element are connected to each other by a material bond. The liquid reservoir and the heating element thereby form a flat composite material. The liquid reservoir, for example made of an open-pore sintered body, acts as a wick and directs the liquid to be vaporized to the heating element. The heating element is applied to one of the surfaces of the liquid reservoir, for example in the form of a coating. Therefore, vaporization again occurs in locally limited manner on the surface, so that there is again a risk of overheating here.

To avoid this problem, vaporizer units are known from the prior art, in which vaporization occurs not only on the surface of the liquid reservoir, but over the entire volume thereof. The vapor is not only produced locally on the surface, but throughout the volume of the liquid reservoir. Thus, the vapor pressure within the liquid reservoir is largely constant, and capillary transport of the liquid to the surface of the liquid reservoir is no longer necessary. Accordingly, the rate of vaporization is no longer minimized by capillary transport. A prerequisite for such a vaporizer is an electrically conductive and porous material. When a voltage is applied, the whole volume of the vaporizer heats up and vaporization occurs everywhere in the volume.

Such vaporizers are described in US 2014/0238424 A1 and in US 2014/0238423 A1. Here, the liquid reservoir and the heating element are combined in one component, for example in the form of a porous body made of metal or a metal mesh. However, a drawback hereof is that the ratio of pore size to electrical resistance cannot be easily adjusted in the described porous bodies. Also, after application of the conductive coating, the coating can be degraded by subsequent sintering.

However, the materials described in the aforementioned prior art are not or only partially suitable to produce composite materials with both, high adjustable porosity and good electrical conductivity, by a sintering process. Moreover, it is generally difficult to continuously coat ceramics, because of their fine porosity and rough surface.

SUMMARY

An object of the invention, therefore, is to provide a sintered body coated with an electrical coating, which is in particular suitable for use as a vaporizer in electronic cigarettes and/or medication administration devices, and/or thermally heated fragrance vaporizers, and which does not exhibit the drawbacks mentioned above. In particular, the invention intends to provide good heatability and easy adjustability of electrical resistance and porosity of the liquid reservoir. Another object of the invention is to provide a method for producing such a coated sintered body.

The vaporizer or vaporizer unit of the invention comprises a sintered body and an electrically conductive coating.

A carrier liquid is stored in the liquid reservoir by adsorptive interactions, which carrier liquid may contain fragrant and flavoring substances and/or medications including active substances and/or nicotine dissolved in suitable liquids, for example. When a voltage is applied, high temperatures are generated in the vaporizer by the electrically conductive coating, so that the carrier liquid is vaporized, desorbed from the wetted surface of the vaporizer, and the vapor can be inhaled by the user.

The sintered body may be made of glass or glass ceramics and has an open porosity in a range from 10 to 90% based on the volume of the sintered body.

Preferably, at least 90%, more particularly at least 95% of the total pore volume are open pores. The open porosity can be determined using measuring methods according to DIN EN ISO 1183 and DIN 66133.

According to one embodiment of the invention, the sintered body has an open porosity in a range from at least 20%, preferably 20% to 90%, more preferably 50% to 80%, and most preferably in a range from 60% to 80%. Due to the high porosity, high adsorption capacity of the sintered body is ensured. According to one embodiment, for example, the sintered body is able, at a temperature of 20° C. and in an adsorption time of 3 hours, to adsorb propylene glycol in an amount of at least 50% of its open pore volume. At the same time, the sintered body has a good mechanical stability. In particular sintered bodies with a relatively low porosity exhibit high mechanical stability, which can be particularly advantageous for some applications. According to another embodiment, open porosity is from 20% to 50%.

The sintered body preferably includes only a small proportion of closed pores. As a result, the sintered body has only a small dead volume, i.e. a volume which does not contribute to the uptake of the liquid to be vaporized. Preferably, the sintered body includes a proportion of closed pores of less than 15% or even less than 10% of the total volume of the sintered body. For determining the proportion of closed pores, the open porosity can be determined as described above. Total porosity is calculated from the density of the body. The proportion of closed pores is then resulting as the difference of total porosity and open porosity. According to one embodiment of the invention, the sintered body even has a proportion of closed pores of less than 5% of the total volume. Closed pores may be formed by pores in the granules which are used for sintering, by the sintering process, or else by coating very small open pores with the electrically conductive coating. Open pores may in particular become closed by the electrically conductive coating if the corresponding pores are very small and/or when the layer thickness of the electrically conductive coating is very thick.

The electrically conductive coating is bonded to the surface of the sintered body preferably by a frictional connection and by a material bond. Not only the pores on the lateral surfaces of the porous sintered body are provided with the electrically conductive coating, but also the pores in the interior of the sintered body. Thus, the open pores are provided with the electrically conductive coating throughout the volume of the sintered body. Consequently, when a voltage is applied to the sintered body coated according to the invention, a current will flow through the entire volume of the sintered body which will therefore be heated throughout its volume. Hence, the electrically conductive coating is deposited on the surface area of the sintered body and bonded to the surface of the sintered body. The electrically conductive coating is thereby lining the pores which are located in the interior of the sintered body, so that when at least a portion or section of the sintered body is electrically connected and a current is applied, this current will flow at least partially through the interior of the sintered body and will heat the interior of the sintered body.

Thus, heating occurs throughout the entire energized volume of the sintered body and, correspondingly, the liquid to be vaporized is vaporized in the entire volume of the sintered body. Vapor pressure is consistent everywhere in the sintered body, and the vapor is not produced merely locally on the surfaces defining the lateral surfaces of the sintered body, but also inside the sintered body. The electrically conductive coating is applied on the surface area of the sintered body and therefore forms at least part of the pore surface thereof.

In contrast to vaporizers which have a localized heating device such as a heating coil or an electrically conductive coating only on the lateral surfaces of the sintered body, capillary transport to the surface of the sintered body is not necessary. This prevents the vaporizer from running dry due to not enough capillary action and thus from local overheating. This has an advantageous effect on the service life of the vaporizer unit. Furthermore, in the event of local overheating of the vaporizer, decomposition processes of the liquid to be vaporized might be caused. This can be problematic, on the one hand, because the content of active substance of a medication to be vaporized is reduced, for example. On the other hand, decomposition products are inhaled by the user, which may imply health risks. In the vaporizer according to the invention, by contrast, this risk does not exist.

Alternatively, heating of the sintered body may as well be effected by inductively or capacitively coupling the electrically conductive coating.

In a preferred embodiment of the invention, the entire surface area of the sintered body as defined by the open pores is covered with the electrically conductive coating. Thus, in a cylindrical sintered body, for example, the term "entire surface" also includes the surface of the sintered body defined by the pores in the interior of the body. The entire coated surface is therefore generally larger than the outer surface of the body.

The coated sintered body may have different geometries, depending on the field of application. For example, the sintered body may have the shape of a solid or hollow cylinder, a sheet-like shape, a prismatic, polyhedral or annular shape. The particular shape can already be determined by the shape of the green body prior to sintering. However, due to the high mechanical stability of the sintered body, machining of the sintered body after sintering is likewise possible.

The electrically conductive coating may in particular consist of a metal such as, for example, silver, gold, platinum, or chromium, or a metal oxide. In one embodiment of the invention, the metal oxide is a metal oxide selected from the group consisting of indium tin oxide (ITO), aluminum-doped zinc oxide (AZO), fluorine tin oxide (FTO), and antimony tin oxide (ATO). Metal oxides have proved to be particularly advantageous here, because of their good adhesion to glass and due to the good wetting behavior of the liquid to be vaporized on the metal oxide. Moreover, the aforementioned metal oxides, in particular ITO, exhibit high chemical and mechanical stability and are insoluble in water and alcohol, so that they are inert towards the solvent of the liquid to be vaporized. In addition, the metal oxides mentioned above are stable to temperatures up to 2000° C. Preferably, the coating contains ITO and/or is an ITO coating.

When used as a vaporizer in electronic cigarettes, the sintered body with the electrically conductive coating preferably has an electrical conductivity in a range from 0.001 to $10^6$ S/m. A conductivity in a range from 10 to 600 S/m has proved to be particularly advantageous. Conductivities in the ranges stated above are particularly advantageous in the case of relatively small vaporizers such as those used in electronic cigarettes. The indicated conductivities are high enough to ensure sufficient heat development for the vaporization. At the same time, excessive heat output powers which might lead to overheating and thus to a decomposition of the liquid components are avoided.

The sintered body according to the invention can be used as a vaporizer in electronic cigarettes, and also as a vaporizer in medical inhalers. The two applications imply different requirements for the vaporizer. This applies in particular to the required heating power of the vaporizer. Electrical resistance and thus the heating power of the vaporizer can be adjusted via the layer thickness of the electrically conductive coating and the electrical conductivity of the coated sintered body achieved in this way. This is advantageous, since the optimum heating power depends on the dimensions of the sintered body and on the voltage source employed in each case. For example, vaporizers that are used in electronic cigarettes have a small size of a few centimeters and are usually operated using one or more voltage sources with a voltage from 1 V to 12 V, preferably with a voltage between 1 and 5 V. These power sources may be standard disposable or rechargeable batteries. According to one embodiment, the vaporizer is operated at an operating voltage in a range from 3 to 5 volts. In this case, electrical resistances in a range from 0.2 to 5 ohms and a heating power of up to 80 W have proved to be particularly advantageous. Inhalers in the medical field, by contrast, may also be operated at voltages of 110 V, 220 V/230 V, or even 380 V, for example. In this case, electrical resistances of up to 3000 ohms and output powers of up to 1000 W are advantageous. Depending on the embodiment of a vaporizer unit or its use, other operating voltages such as, for example, between more than 12 V and less than 110V, and resistances of more than 5 ohms, for example, and power ranges of more than 80 W, for example, may be appropriate.

According to one embodiment of the invention, the layer thickness of the electrically conductive coating is in a range from 1 nm to 800 μm. Layer thicknesses in a range from 200 nm to 200 μm or 200 nm to 10 μm have proved to be particularly advantageous. If the coating has an excessive thickness, there is a risk of pores becoming closed by the electrically conductive coating. The layer thickness furthermore depends on the employed material. For example, layers based on metal oxides usually have a significantly greater thickness than metal layers.

According to one embodiment of the invention, an electrically conductive coating of a deposited metal, for example silver, gold, platinum or chromium, is provided in a layer thickness ranging from 1 nm to 1 μm, preferably from 10 nm to 100 nm.

The electrically conductive coating may have a homogeneous layer thickness within the sintered body. However, sintered bodies with an electrically conductive coating of inhomogeneous layer thickness within the sintered body are likewise covered by the subject-matter of the present invention. This applies in particular to coatings based on metal oxides and having a relatively large layer thickness. According to one embodiment of the invention, the layer thickness of the electrically conductive coating has a gradient within the sintered body. For example, the layer thickness may decrease from the outside to the inside.

In addition to the layer thickness described above, the desired electrical resistance may be adjusted through the electrical conductivity of the coated sintered body. The electrical conductivity of the coated sintered body depends on the employed coating material or its electrical conductivity. In one embodiment of the invention, the coated sintered body exhibits an electrical conductivity from 0.001 to $10^6$ S/m, preferably from 10 to 600 S/m.

According to one embodiment of the invention, the pores have an average pore size in a range from 1 μm to 5000 μm. Preferably, the pore size of the open pores of the sintered body is in a range from 100 to 800 μm, most preferably in a range from 200 to 600 μm. Pores of such size are advantageous, as they are small enough to produce sufficiently large capillary force to ensure resupply of the liquid to be vaporized, especially during operation of the vaporizer, and at the same time large enough to allow rapid release of the vapor. If the pores are too small, they risk to become completely or partially closed up by the electrically conductive coating.

According to one embodiment of the invention, an at least bimodal distribution of the pore sizes is contemplated. In this case, the sintered body has small pores and large pores, with a respective discrete pore size distribution. The small pores provide for a large capillary force and thus for good and rapid uptake of the liquid in the sintered body. However, since small pores will release the vapor rather slowly, the sintered body additionally has large pores providing for a rapid release of the vapor. The pore size and the ratio of large pores to small pores can be adjusted via the production process of the sintered body by using salts of different grain sizes in the corresponding ratio, as pore formers. Through the ratio of large pores to small pores it is possible to adjust the adsorption or desorption behavior of the sintered body. Depending on the application, the proportion of large pores is in a range from 5 to 95% of the total number of pores. This refinement of the invention preferably comprises small pores in a range from 100 to 300 μm and large pores in a range from 500 to 700 μm.

According to one embodiment of the invention, the sintered body is made of glass. Glasses with a rather low alkali content have proved to be particularly advantageous here. A low alkali content, in particular a low content of sodium, is advantageous for several reasons. On the one hand, such glasses have a rather high transition temperature $T_g$, so that, once the electrically conductive coating has been applied, it can be fired at rather high temperatures. In particular in the case of electrically conductive coatings based on oxides, high firing temperatures have a favorable effect on the density of the electrically conductive coating and on the electrical conductivity of the sintered body. Preferably, the glasses have a transition temperature $T_g$ in a range from 300° C. to 900° C., preferably from 500° C. to 800° C.

On the other hand, glasses with a rather low alkali content exhibit low alkali diffusion even at high temperatures, so that sintering can be performed and the coating can be fired at rather high temperatures, without adversely altering it or its properties. The low alkali diffusion of the glasses is moreover advantageous during operation of the sintered body as a vaporizer, since there will be no released constituents interacting with the electrically conductive coating or with the liquid to be vaporized. The latter is particularly relevant when the coated sintered body is used as a vaporizer in medical inhalers. An alkali content of the glass of not more than 11 wt % or even not more than 6 wt % has been found to be particularly advantageous.

The sintered body is subjected to large temperature variations, both during its manufacture and during operation. During operation of the vaporizer, this is caused by numerous heating cycles. Hence, besides mechanical resistance, the sintered body must also exhibit high thermal resilience. Therefore, it is preferable for the sintered body to have a coefficient of linear thermal expansion $\alpha_{20\text{-}300°\ C.\_sintered\ body}$ of less than $11*10^{-6}$ K$^{-1}$, preferably less than $8*10^{-6}$ K$^{-1}$. In order to keep thermal stresses between the sintered body and the electrically conductive coating as low as possible, it may be favorable, depending on the coating, if the sintered body has a coefficient of linear thermal expansion $\alpha_{20\text{-}300°\ C.}$ in a range from 1 to $10*10^{-6}$ K$^{-1}$, the electrically conductive coating has a coefficient of linear thermal expansion $\alpha_{20\text{-}300°\ C.\_coating}$ in a range from 1 to $20*10^{-6}$ K$^{-1}$, and/or if the difference of the two coefficients of thermal expansion $\Delta\alpha_{20\text{-}300°\ C.}=\alpha_{20\text{-}300°\ C.\_coating}-\alpha_{20\text{-}300°\ C.\_sintered\ body}$ is from 0 to $20*10^{-6}$ K$^{-1}$, preferably from 0 to $10*10^{-6}$ K$^{-1}$, also preferred from 0 to $5*10^{-6}$ K$^{-1}$.

One embodiment of the invention proposes a metallic electrically conductive coating, preferably a silver coating, and a sintered body made of glass with a linear coefficient of thermal expansion in a range from $8*10^{-6}$ K$^{-1}$ to $20*10^{-6}$ K$^{-1}$.

According to one embodiment of the invention, the coated sintered body has an electrically conductive coating made of ITO and a sintered glass body with a coefficient of linear thermal expansion in a range from $3*10^{-6}$ K$^{-1}$ to $8*10^{-6}$ K$^{-1}$. Such coefficients of thermal expansion or differences thereof have been found to be advantageous in particular when electrically conductive coatings based on metal oxide are employed. These coatings are usually applied to the sintered body in a greater thickness than metallic coatings, for example.

Surprisingly, despite the differences in $\alpha_{20\text{-}300°\ C.}$ of the glass and the coating, it is possible to obtain crack-free or at least low-crack layers of rather large layer thicknesses even if metal oxides are used as the electrically conductive coating. Crack-free or low-crack layers can in particular be obtained if, after deposition thereof on the sintered body, they are fired at high temperatures, preferably at temperatures in a range from 300 to 900° C. It has been found that such ITO coatings do not tend to cracking or delamination, even during operation of a vaporizer, i.e. under a cyclic thermal load. Thus, the electrical conductivity of the coated sintered body will remain constant or at least substantially constant over the service life of the vaporizer, and therefore also the vaporization performance of the vaporizer. A further advantage of a low-crack coating is that even during operation of the vaporizer, no release of metal oxide and/or glass particles or flakes, in particular of a particle size of less than 5 μm will arise, which could otherwise be inhaled by the user.

According to another embodiment of the invention, the electrically conductive coating and/or an intermediate zone toward the sintered body exhibits a gradient with respect to the coefficient of linear thermal expansion. The coefficient of linear thermal expansion thereby increases from the interface of the coating in contact with the sintered body to the free surface of the coating. With such a $\alpha_{20\text{-}300°\ C.}$ gradient of the electrically conductive coating, thermal stresses between the sintered body and the coating can be compensated.

Preferably, the sintered body has a lower $\alpha_{20\text{-}300°\ C.}$ than the electrically conductive coating. This ensures that the coating is not subjected to tensile stress during heating operation. Tensile stress on the coating might have an adverse effect in terms of formation of cracks in the coating or enlargement of existing cracks and/or delamination of the layer.

Since, due to the configuration of the vaporizer according to the invention as a volumetric vaporizer, there will be no localized overheating, for example at the surface or in the areas which are close to and/or in direct contact with a heating element or parts of a heating element in conventional vaporizers, and since, therefore, lower maximum temperatures will be reached than in vaporizers known from the prior art, a variety of glasses is suitable. Due to the associated choice of various different glasses, the respective suitable glass can be selected for each particular electrically conductive coating that is used, with regard to thermal expansion coefficients, chemical resistance, or feasible firing temperature.

Furthermore, when the coated sintered body is employed as a vaporizer in an electronic cigarette or as a medical inhaler, any release of substances from the glass that might potentially be dangerous for the user should be excluded. Therefore, the glasses that are preferably used do not contain the following elements, or only in very small unavoidable traces: arsenic, antimony, cadmium, and/or lead. More particularly, the content of arsenic, antimony, cadmium, and/or lead is less than 500 ppm.

One embodiment of the invention proposes the following glass composition for the porous sintered body, in wt %:

| | |
|---|---|
| $SiO_2$ | 30 to 85 |
| $B_2O_3$ | 3 to 20 |
| $Al_2O_3$ | 0 to 15 |
| $Na_2O$ | 3 to 15 |
| $K_2O$ | 3 to 15 |
| $ZnO$ | 0 to 12 |
| $TiO_2$ | 0.5 to 10 |
| $CaO$ | 0 to 0.1. |

In a further embodiment of the invention, the glass of the porous sintered body has the following composition, in wt %:

| | |
|---|---|
| $SiO_2$ | 58 to 65 |
| $B_2O_3$ | 6 to 10.5 |
| $Al_2O_3$ | 14 to 25 |
| $MgO$ | 0 to 3 |
| $CaO$ | 0 to 9 |
| $BaO$ | 3 to 8 |
| $ZnO$ | 0 to 2, | with a total of the contents of MgO, CaO, and BaO being in a range from 8 to 18 wt %.

In a further embodiment of the invention, the glass of the porous sintered body has the following composition, in wt %:

| | |
|---|---|
| $SiO_2$ | 61 |
| $B_2O_3$ | 10 |
| $Al_2O_3$ | 18 |
| $MgO$ | 2.8 |
| $CaO$ | 4.8 |
| $BaO$ | 3.3. |

Glasses of this embodiment have the following properties:

| | |
|---|---|
| $\alpha_{(20\text{-}300° C.)}$ | $3.2 * 10^{-6}/K$ |
| $T_g$ | 717° C. |
| Density | 2.43 g/cm³. |

According to a further embodiment of the invention, the porous sintered body has the following glass composition, in wt %:

| | |
|---|---|
| $SiO_2$ | 55 to 75 |
| $Na_2O$ | 0 to 15 |
| $K_2O$ | 2 to 14 |
| $Al_2O_3$ | 0 to 15 |
| $MgO$ | 0 to 4 |
| $CaO$ | 3 to 12 |
| $BaO$ | 0 to 15 |
| $ZnO$ | 0 to 5 |
| $TiO_2$ | 0 to 2. |

One embodiment proposes a sintered body with the following glass composition, in wt %:

| | |
|---|---|
| $SiO_2$ | 64-74 |
| $Na_2O$ | 6-10 |
| $K_2O$ | 6-10 |
| $CaO$ | 5-9 |
| $BaO$ | 0-4 |
| $ZnO$ | 2-6 |
| $TiO_2$ | 0-2. |

With glasses in this range of composition, a porous glass body with the following properties can be obtained:

| | |
|---|---|
| $\alpha_{(20\text{-}300° C.)}$ | $9.4 * 10^{-6}/K$ |
| $T_g$ | 533° C. |
| Density | 2.55 g/cm³. |

A further embodiment proposes a porous glass body with the following composition, in wt %:

| | |
|---|---|
| $SiO_2$ | 75-85 |
| $B_2O_3$ | 8-18 |
| $Al_2O_3$ | 0.5-4.5 |
| $Na_2O$ | 1.5-5.5 |
| $K_2O$ | 0-2. |

With this composition, a porous glass body with the following properties can be obtained:

| | |
|---|---|
| $\alpha_{(20\text{-}300° C.)}$ | $3.25 * 10^{-6}/K$ |
| $T_g$ | 525° C. |
| Density | 2.2 g/cm³. |

In a further embodiment of the invention, the glass of the porous sintered body has the following composition, in wt %:

| | |
|---|---|
| $SiO_2$ | 50 to 65 |
| $Al_2O_3$ | 15 to 20 |
| $B_2O_3$ | 0 to 6 |
| $Li_2O$ | 0 to 6 |
| $Na_2O$ | 8 to 15 |
| $K_2O$ | 0 to 5 |
| $MgO$ | 0 to 5 |
| $CaO$ | 0 to 7, preferably 0 to 1 |
| $ZnO$ | 0 to 4, preferably 0 to 1 |
| $ZrO_2$ | 0 to 4 |
| $TiO_2$ | 0 to 1, preferably free of $TiO_2$. |

Furthermore, the glass may contain 0 to 1 wt % of $P_2O_5$, SrO, BaO, as well as 0 to 1 wt % of refining agents $SnO_2$, $CeO_2$, or $As_2O_3$, F, Cl, sulfate, or other refining agents.

According to one embodiment of the invention, the glass of the porous sintered body is a ceramizable lithium aluminosilicate glass. One embodiment proposes the following glass composition, in wt %:

| | |
|---|---|
| SiO$_2$ | 55-69 |
| Al$_2$O$_3$ | 15-25 |
| Li$_2$O | 3-5 |
| Na$_2$O + K$_2$O | 0-30 |
| MgO + CaO + SrO + BaO | 0-5 |
| ZnO | 0-4 |
| TiO$_2$ | 0-5 |
| ZrO$_2$ | 0-5 |
| TiO$_2$ + ZrO$_2$ + SnO$_2$ | 2-6 |
| P$_2$O$_5$ | 0-8 |
| F | 0-1 |
| B$_2$O$_3$ | 0-2 |
| $\alpha_{20\text{-}300°\,C.}$ | 3.3-5.7 in the form of glass. |

The glass has a $\alpha_{20\text{-}300°\,C.}$ in a range from $3.3*10^{-6}$ K$^{-1}$ to $5.7*10^{-6}$ K$^{-1}$.

Alternatively, the glass of the porous sintered body has the following composition, in wt %:

| | |
|---|---|
| SiO$_2$ | 57-66 |
| Al$_2$O$_3$ | 15-23 |
| Li$_2$O | 3-5 |
| Na$_2$O + K$_2$O | 3-25 |
| MgO + CaO + SrO + BaO | 1-4 |
| ZnO | 0-4 |
| TiO$_2$ | 0-4 |
| ZrO$_2$ | 0-5 |
| TiO$_2$ + ZrO$_2$ + SnO$_2$ | 2-6 |
| P$_2$O$_5$ | 0-7 |
| F | 0-1 |
| B$_2$O$_3$ | 0-2. |

The glass of this embodiment has a $\alpha_{20\text{-}300°\,C.}$ in a range from $4.7*10^{-6}$ K$^{-1}$ to $5.7*10^{-6}$ K$^{-1}$.

The following glass composition, in wt %, has proved to be particularly advantageous:

| | |
|---|---|
| SiO$_2$ | 57-63 |
| Al$_2$O$_3$ | 15-22 |
| Li$_2$O | 3.5-5 |
| Na$_2$O + K$_2$O | 5-20 |
| MgO + CaO + SrO + BaO | 0-5 |
| ZnO | 0-3 |
| TiO$_2$ | 0-3 |
| ZrO$_2$ | 0-5 |
| TiO$_2$ + ZrO$_2$ + SnO$_2$ | 2-5 |
| P$_2$O$_3$ | 0-5 |
| F | 0-1 |
| B$_2$O$_3$ | 0-2. |

Another embodiment of the invention proposes to use a porous sintered body made of soda-lime glass. More particularly, the soda-lime glass is a glass having the following composition, in wt %:

| | |
|---|---|
| SiO$_2$ | 40-81 |
| Al$_2$O$_3$ | 0-6 |
| B$_2$O$_3$ | 0-5 |
| Li$_2$O + Na$_2$O + K$_2$O | 5-30 |
| MgO + CaO + SrO + BaO + ZnO | 5-30 |
| TiO$_2$ + ZrO$_2$ | 0-7 |
| P$_2$O$_5$ | 0-2. |

Glasses of this embodiment have a $\alpha_{20\text{-}300°\,C.}$ in a range from $5.5*10^{-6}$ K$^{-1}$ to $9.7*10^{-6}$ K$^{-1}$.

Preferably, a soda-lime glass of the following composition, in wt %, is used for the porous sintered body:

| | |
|---|---|
| SiO$_2$ | 50-81 |
| Al$_2$O$_3$ | 0-5 |
| B2O3 | 0-5 |
| Li$_2$O + Na$_2$O + K$_2$O | 5-28 |
| MgO + CaO + SrO + BaO + ZnO | 5-25 |
| TiO$_2$ + ZrO$_2$ | 0-6 |
| P$_2$O$_5$ | 0-2. |

Glasses of this embodiment have a $\alpha_{20\text{-}300°\,C.}$ in a range from $4.9*10^{-6}$ K$^{-1}$ to $10.3*10^{-6}$ K$^{-1}$.

In a particularly preferred refinement of this embodiment, the porous sintered glass body consists of a soda-lime glass of the following composition, in wt %:

| | |
|---|---|
| SiO$_2$ | 55-76 |
| Al$_2$O$_3$ | 0-5 |
| B$_2$O$_3$ | 0-5 |
| Li$_2$O + Na$_2$O + K$_2$O | 5-25 |
| MgO + CaO + SrO + BaO + ZnO | 5-20 |
| TiO$_2$ + ZrO$_2$ | 0-5 |
| P$_2$O$_5$ | 0-2. |

According to a further embodiment, the glass of the sintered body contains the following constituents, in wt %:

| | |
|---|---|
| SiO$_2$ | 1 to 85 |
| B$_2$O$_3$ | 0 to 60 |
| Al$_2$O$_3$ | 0 to 30 |
| Li$_2$O | 0 to 5 |
| Na$_2$O | 0 to 20 |
| K$_2$O | 0 to 15 |
| ZnO | 0 to 62 |
| TiO$_2$ | 0 to 10 |
| CaO | 0 to 35 |
| BaO | 0 to 60 |
| MgO | 0 to 10 |
| SrO | 0 to 30 |
| La$_2$O$_3$ | 0 to 40 |
| Fe$_2$O$_3$ | 0 to 10 |
| MnO2 | 0 to 5 |
| Bi$_2$O$_3$ | 0 to 85 |
| Cs$_2$O | 0 to 20 |
| SnO | 0 to 5 |
| ZrO$_2$ | 0 to 10 |
| Y$_2$O$_3$ | 0 bis 15 |
| F | 0 bis 7. |

According to one embodiment, the glasses may contain color-imparting oxides such as Nd$_2$O$_3$, Fe$_2$O$_3$, CoO, NiO, V$_2$O$_5$, MnO$_2$, TiO$_2$, CuO, and/or CeO$_2$. Alternatively or additionally, 0 to 2 wt % of As$_2$O$_3$, Sb$_2$O$_3$, SnO$_2$, SO$_3$, Cl, F, and/or CeO$_2$ may be added as a refining agent.

Another embodiment proposes to add pigments to the glass, alternatively or additionally.

In one embodiment of the invention, the coated sintered body has one or more further coatings in addition to the electrically conductive coating. For example, a coated sintered body which has been coated galvanically with a metal as the electrically conductive layer may have a so-called starter coating between the surface of the sintered body and the electrically conductive metal layer.

If metals are used as an electrically conductive coating and a sintered body made of glass, the problem may arise that the surface tensions of glass and metal can differ significantly so that good adhesion of the electrically conductive coating on the glass surface may be difficult to achieve. One embodiment of the invention therefore proposes to apply an oxidic layer between the sintered body and the metallic coating. This layer is effective as an adhesion promoter, so that particularly good adhesion of the metallic coating can be achieved. Furthermore, an additional coating of the surface of the sintered body can be used to alter the zeta potential of the surface so as to adapt it to the zeta potential of the liquid to be vaporized. Alternatively or additionally, it is also possible to deposit a further layer on the electrically conductive coating, for example a protective layer or passivation layer.

Alternatively or additionally, the electrically conductive coating or the body may contain a further component, for example an antibacterial and/or antimicrobial component. Suitable antibacterial or antimicrobial components include silver, ZnO, and $TiO_2$, inter alia. Silver as a component of the conductive coating has the advantage of being conductive on the one hand and of additionally having an antibacterial effect on the other hand.

The sintered body coated according to the invention can be used as a heating element in a vaporizer. In this case, the required electronic connections can be established mechanically, for example by spring forces or by a positive connection, or by a material bond, for example by a solder joint. A silver conductive paste may be used as a solder, for example. Establishing connections via intermediate layers is likewise possible.

Such a vaporizer may be a component of an electronic cigarette, for example, or of a medical inhaler, a fragrance dispenser, a room humidifier, or of a device for dispensing substances such as, e.g., insecticides or insect repellents, or for similar applications.

Furthermore, the invention relates to a method for producing a sintered body coated with an electrically conductive coating. The method according to the invention comprises at least the following method steps: (a) providing a sintered body made of glass or glass ceramics and having an open porosity in a range from 10 to 90%; and (b) coating the surface of the sintered body as defined by the open pores, including the surface of pores in the interior of the sintered body, with an electrically conductive coating.

The providing of the sintered body in step (a) can be achieved by a process in which, first, fine-grained glass powder with a mean grain size in a range of approximately 20 μm to 600 μm, preferably not more than 300 μm, is mixed with a high-melting salt and a binder. The grain size of the salt that is used is adapted to the desired pore size of the sintered body. Then, 5 to 80 wt % of fine-grained glass powder is added to this mixture and the mass is pressed into shape. The resulting shaped body is heated to the sintering temperature of the glass and sintered. The melting temperature of the employed salt is above the respective sintering temperature, so that the grain structure of the salt is preserved. Following the sintering process, the salt is washed out with a suitable solvent. The salts NaCl and $K_2SO_4$ have been found to be particularly suitable for this purpose. Other salts such as KCl, $MgSO_4$, $Li_2SO_4$, $Na_2SO_4$ are conceivable as well. Besides such aspects as costs, environmental compatibility or the like, the choice of the salt is determined by the glass that is employed and the temperature required for sintering it. According to one embodiment of the invention, 20 to 85 wt % of salt with a grain size from 30 to 5000 μm is thoroughly mixed with 5 to 85 wt % of glass powder having a grain size from 1 to 500 μm and with an aqueous polyethylene glycol solution. The so obtained mixture can either be dried, or 5 to 80 wt % of glass powder (based on the mass of the mixture) can be added thereto in the moist state. The mixture is pressed into shape and sintered at the sintering temperature of the employed glass. Subsequently, the salt is washed out so that a porous sintered body is obtained.

As a result, a highly porous sintered body with open pores is obtained. Since the individual glass grains are firmly bonded to each other by the sintering process, the sintered body exhibits good mechanical strength, despite of its high porosity, when compared to a corresponding glass fiber material such as a fiberglass rope wick. Thus, the sintered body does not contain any loose or easily releasable particles which might be inhaled by the user when the sintered body is used as a liquid reservoir in an electronic cigarette and/or in a medication administering device and/or in thermally heated vaporizers for fragrant substances. Due to the high mechanical stability of the sintered body, it is thus possible to provide liquid reservoirs which may even exhibit a porosity of more than 80 vol %.

In one embodiment of the invention, a sintered glass body is provided in step (a). A sintered glass body with an alkali content of less than 15 wt %, preferably less than 10 wt %, and most preferably less than 5 wt % has proved to be advantageous. Glasses with such a low alkali content have a high softening temperature, so that the sintering in step (a) can be performed at high temperatures. Aluminosilicate glasses and borosilicate glasses have proved to be particularly advantageous.

In step (b), the electrically conductive layer can be deposited on the surface of the sintered body by condensation or precipitation of solids from a dispersion, by condensation or precipitation of solids from a solution (e.g. sol-gel), by condensation or precipitation of solids from the gas phase, or by a galvanic process. The respective coating method depends on the coating material that is used and on the desired layer thickness.

In one embodiment of the invention, a metallic layer is deposited electrolytically. For example, a silver coating can be deposited on the porous sintered body by deposition from a silver solution. The silver content of the solution used for this purpose is preferably form 10 to 20 wt % or from 15 to 20 wt %. Alternatively, silver can be deposited by reduction from a solution, for example by reduction of a silver nitrate solution with sugar, or by precipitation reactions.

According to one embodiment of the inventive method it is contemplated that in step (b) an electrically conductive coating is applied in the form of a metal oxide selected from indium tin oxide (ITO), aluminum-doped zinc oxide (AZO), fluorine tin oxide (FTO), and antimony tin oxide (ATO). Preferably, in step (b), the metal oxide is deposited by condensation or precipitation from a solution or dispersion, most preferably from a dispersion.

Coating of the sintered body by a dipping process has proved to be particularly advantageous. In a corresponding embodiment of the aforementioned variation of the invention, the dipping process comprises at least the following method steps: (a2) providing the sintered body; (b2) providing a dispersion or solution of the metal oxide; (c2) immersing the sintered body into the dispersion provided in step (b2) for a predefined dipping time $t_{dip}$; (d2) drying the coated sintered body obtained in step (c2); (e2) firing the coating obtained by steps (c2) and (d2) for a firing time $t_{fire}$ at a predefined firing temperature $T_{fire}$.

The layer thickness of the electrically conductive coating deposited by a dipping process is preferably from 200 nm to 200 μm, more preferably from 200 nm to 10 μm, and can be adjusted via the solids content of the dispersion or solution employed in step (b). Preferably, the solids content is from 1 to 50 wt %, most preferably from 20 to 35 wt %.

Alternatively or additionally, the desired layer thickness of the deposited layer can be achieved through the number of immersion repetitions of the sintered body. For example, one embodiment proposes that steps (c2) and (d2) are performed repeatedly, preferably 2 to 3 times. In a further embodiment of the invention, the sintered body is immersed for different lengths of time during the several dipping operations. In this manner it is possible to obtain a gradient in electrical conductivity of the coating.

In step (e2), the layer is preferably fired at a firing temperature $T_f s$, in a range from 60 to 1000° C., most preferably in a range from 300 to 900° C. Especially with high firing temperatures it is possible to obtain very dense layers. In this manner, low-crack or even crack-free coatings can be obtained even in case of large layer thicknesses. Even in the case of differing $\alpha_{20\text{-}300°\ C.}$ of the sintered body and the coating, the coating remains low in or free of cracks under cyclic thermal stress. It is believed that due to the high firing temperatures a diffusion zone is formed between the metal oxide and the sintered body, which compensates for the differences in $\alpha_{20\text{-}300°\ C.}$. The firing of the electrically conductive coating in step (e2) may be performed under inert gas, under vacuum, or under a slightly reducing atmosphere, such as a 3 to 50% hydrogen atmosphere, or under carbon monoxide.

The method described above or its embodiments described above can also be used for coating porous ceramics. In this case, a porous sintered ceramic body is provided in step (a) instead of a sintered glass or glass ceramic body. It has proved to be advantageous in this case if the provided ceramic exhibits an identical or at least similar porosity and/or pore size as the described porous bodies made of glass or glass ceramics.

The electrically conductive layers deposited on the pore surface of a porous ceramic using this method are comparable to the electrically conductive layers of the sintered glass or glass ceramic bodies of the invention. This applies in particular with regard to features such as the electrically conductive materials that are used, layer thicknesses, electrical conductivities, and/or electrical resistances of the electrically conductive layers.

Furthermore, a vaporizer head comprising a sintered body according to the invention is also included in the subject-matter of the present invention. This vaporizer head comprises at least a housing, the sintered body according to the invention, and electrical contacts for connecting the sintered body to an electrical power source.

DETAILED DESCRIPTION

The patent or application file contains at least one drawing executed in color. Copies of this patent or patent application publication with color drawing(s) will be provided by the Office upon request and payment of the necessary fee.

The invention will now be described in more detail with reference to exemplary embodiments and the figures, wherein.

DETAILED DESCRIPTION

Figure 1:
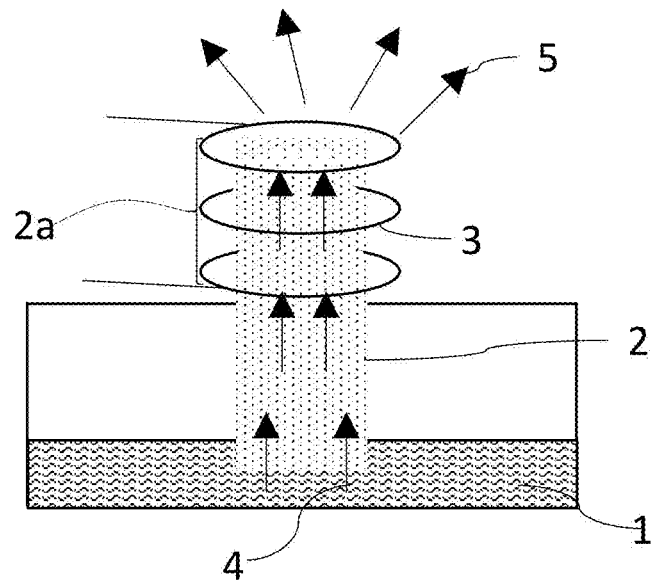
FIG. 1 is a schematic view of a conventional vaporizer.

Tables 1 and 2 show the compositions of the porous sintered body according to various exemplary embodiments. Due to their different composition, the individual exemplary embodiments have different thermal expansion coefficients. For example, exemplary embodiments 8 to 10 have expansion coefficients in a range from $3.2*10^{-6}$ $K^{-1}$ to $3.8*10^{-6}$ $K^{-1}$ and are particularly suitable for porous sintered bodies with an electrically conductive coating based on a metal oxide, e.g. ITO. Moreover, glasses 8 to 10 are free or at least substantially free of sodium, which has an effect not only on the thermal expansion coefficient but also on the glass transition temperatures $T_g$, which are above 700° C. and therefore allow for high firing temperatures during the coating process with ITO, so that it is possible to obtain crack-free or at least largely crack-free electrically conductive coatings of particularly high mechanical stability.

Glasses 2 to 7, by contrast, have a relatively high content of sodium and, accordingly, higher coefficients of thermal expansion. They are therefore particularly suitable for producing porous sintered bodies to be coated with a metallic coating. Furthermore, due to their high content of sodium, the glasses of exemplary embodiments 2 to 7 lend themselves for being chemically toughened. For example, the sintered body may be chemically toughened prior to being coated. This increases the mechanical stability of the porous sintered body.

TABLE 1

| EXEMPLARY EMBODIMENTS 1 TO 7 | | | | | | | |
|---|---|---|---|---|---|---|---|
| | 1 | 2 | 3 | 4 | 5 | 6 | 7 |
| $SiO_2$ | 64.0 | 62.3 | 62.2 | 52 | 60.7 | 62 | 61.1 |
| $B_2O_3$ | 8.3 | | 0.2 | | | | 4.5 |
| $Al_2O_3$ | 4.0 | 16.7 | 18.1 | 17 | 16.9 | 17 | 19.6 |
| $Li_2O$ | | | 5.2 | | | | |

TABLE 1-continued

EXEMPLARY EMBODIMENTS 1 TO 7

|  | 1 | 2 | 3 | 4 | 5 | 6 | 7 |
|---|---|---|---|---|---|---|---|
| $Na_2O$ | 6.5 | 11.8 | 9.7 | 12 | 12.2 | 13 | 12.1 |
| $K_2O$ | 7.0 | 3.8 | 0.1 | 4 | 4.1 | 3.5 | 0.9 |
| SrO |  |  | 0.1 |  |  |  |  |
| CaO |  |  | 0.6 | 6 |  | 0.3 | 0.1 |
| $SnO_2$ |  |  |  |  | 0.4 | 0.1 | 0.2 |
| $TiO_2$ | 4.0 | 0.8 |  |  |  | 0.6 |  |
| $Sb_2O_3$ | 0.6 |  |  |  |  |  |  |
| $As_2O_3$ |  | 0.7 |  |  |  |  |  |
| $Cl^-$ | 0.1 |  |  |  |  |  |  |
| $P_2O_5$ |  |  | 0.1 |  |  |  |  |
| MgO |  | 3.7 |  | 4 |  | 1.2 |  |
| $ZrO_2$ |  | 0.1 | 3.6 | 1.5 | 1.5 |  |  |
| $CeO_2$ |  | 0.1 |  |  | 0.3 |  | 0.3 |
| ZnO | 5.5 |  | 0.1 | 3.5 |  |  |  |
| $T_g$ [° C.] |  | 607 | 505 | 556 | 623 |  | 600 |
| $\alpha_{(20\text{-}300° C.)}$ [$K^{-1}$] |  | $8.6 * 10^{-6}$ | $8.5 * 10^{-6}$ | $9.7 * 10^{-6}$ | $8.3 * 10^{-6}$ |  | $8.9 * 10^{-6}$ |
| Density [$g/cm^3$] |  | 2.4 | 2.5 | 2.6 | 2.4 |  | 2.4 |

TABLE 2

EXEMPLARY EMBODIMENTS 8 TO 12

|  | 8 | 9 | 10 | 11 | 12 |
|---|---|---|---|---|---|
| $SiO_2$ | 59.7 | 58.8 | 62.5 | 74.3 | 72.8 |
| $B_2O_3$ | 7.8 | 10.3 | 10.3 |  |  |
| $Al_2O_3$ | 17.1 | 14.6 | 17.5 | 1.3 | 0.2 |
| $Li_2O$ |  |  |  |  |  |
| $Na_2O$ |  |  |  | 13.2 | 13.9 |
| $K_2O$ |  |  |  | 0.3 | 0.1 |
| SrO | 7.7 | 3.8 | 0.7 |  |  |
| BaO | 0.1 | 5.7 |  |  |  |
| CaO | 4.2 | 4.7 | 7.6 | 10.7 | 9.0 |
| $SnO_2$ |  |  |  |  |  |
| $TiO_2$ |  |  |  |  |  |
| $Sb_2O_3$ |  | 0.2 |  |  |  |
| $As_2O_3$ |  | 0.7 |  |  |  |
| $Cl^-$ |  |  |  |  |  |
| $P_2O_5$ |  |  |  |  |  |
| MgO |  | 1.2 | 1.4 | 0.2 | 4.0 |
| $ZrO_2$ |  |  |  |  |  |
| $CeO_2$ |  |  |  |  |  |
| ZnO |  |  |  |  |  |
| $T_g$ [° C.] | 719 | 705 |  | 573 | 564 |
| $\alpha_{(20\text{-}300° C.)}$ [$K^{-1}$] | $3.8 * 10^{-6}$ | $3.73 * 10^{-6}$ | $3.2 * 10^{-6}$ | $9 * 10^{-6}$ | $9.5 * 10^{-6}$ |
| Density [$g/cm^3$] | 2.51 | 2.49 | 2.38 |  |  |

FIG. 1 shows an example of a conventional vaporizer comprising a porous sintered body 2 as a liquid reservoir. Due to the capillary forces of the porous sintered body 2, the liquid 1 to be vaporized is taken up by the porous sintered body 2 and is further conveyed in all directions of the sintered body 2. The capillary forces are symbolized by arrows 4. In the upper portion of sintered body 2, a heating coil 3 is positioned such that the corresponding area 2a of the sintered body 2 is heated by heat radiation. The heating coil 3 is therefore brought very close to the lateral surfaces of the sintered body 2 and should preferably not touch the lateral surfaces. In practice, however, a direct contact between heating wire and lateral surface is often unavoidable.

Vaporization of the liquid 1 occurs in the heated area 2a. This is illustrated by arrows 5. The vaporization rate depends on the temperature and the ambient pressure. The higher the temperature and the lower the pressure, the faster the liquid will be vaporized in heated area 2a.

Since vaporization of the liquid 1 occurs only locally, on the lateral surfaces of the heated area 2a of the sintered body, this local area has to be heated with relatively high heating powers in order to achieve rapid vaporization within 1 to 2 seconds. Therefore, high temperatures of more than 200° C. must be employed. However, high heating output power, especially in a localized area, can lead to local overheating and thus possibly to a decomposition of the liquid 1 to be vaporized and of the material of the liquid reservoir or of the wick.

Furthermore, high heating output power can also lead to vaporization at an excessive rate, so that more liquid 1 for vaporization cannot be supplied quickly enough by the capillary forces. This also results in overheating of the lateral surfaces of the sintered body in the heated area 2a. Therefore, a unit such as a control or regulation unit (not shown) for voltage, power and/or temperature adjustment may be incorporated, but at the expense of battery life and limiting the maximum amount of vaporization.

Drawbacks of the vaporizer illustrated in FIG. 1 and known from the prior art, therefore, include the technique of localized heating and the associated ineffective heat transfer, the complex and expensive control unit, and the risk of overheating and decomposition of the liquid to be vaporized.

Figure 2:
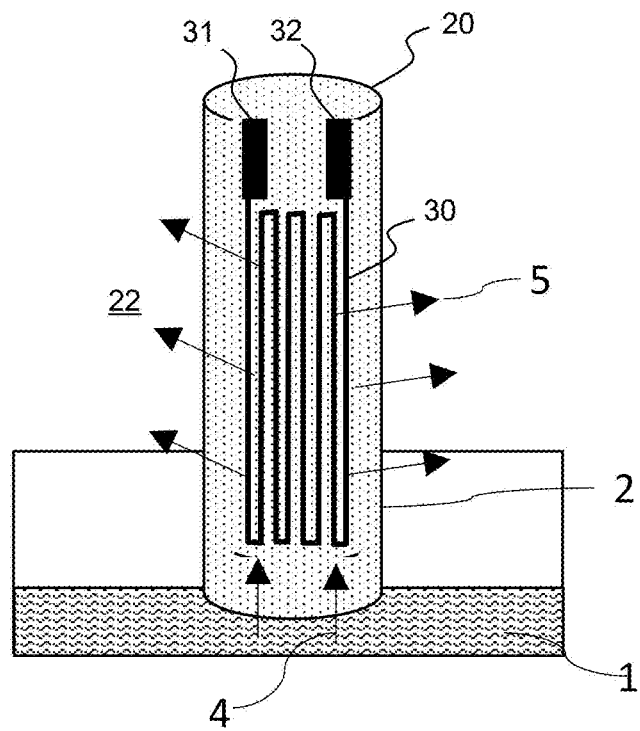
FIG. 2 is a schematic view of a sintered body with electrical contacts on the lateral surfaces of the sintered body.

FIG. 2 shows a vaporizer unit known from the prior art, in which the heating element 30 is disposed directly on the sintered body 20. More particularly, the heating element 30 is firmly connected to the sintered body 20. Such a connection can in particular be achieved if the heating element 30 is provided in the form of a sheet resistor. For this purpose, an electrically conductive sheet resistor type coating patterned in the form of a conductive path is applied onto the sintered body 20. A coating that is directly applied to the sintered body 20 as a heating element 30 is advantageous in order to achieve good thermal contact which provides for fast heating, inter alia. However, the vaporizer unit shown in FIG. 2 also presents only a locally limited vaporization surface, so that there is again a risk of overheating of the surface here.

Figure 3:
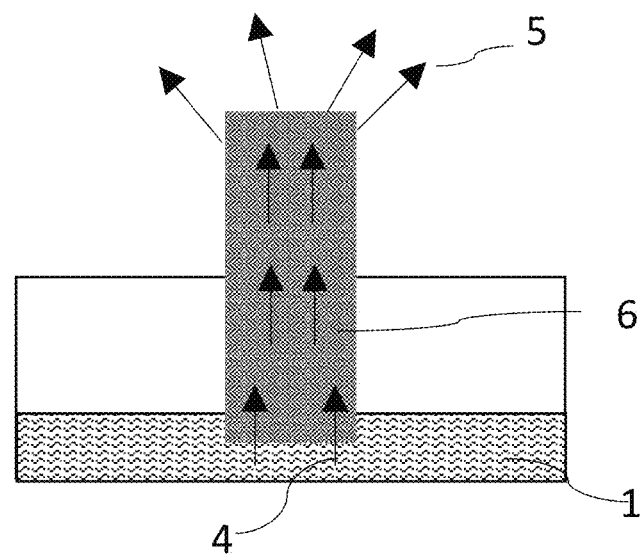
FIG. 3 is a schematic view of a vaporizer comprising a sintered body coated according to the invention, as a heating element.

FIG. 3 schematically shows the configuration of a vaporizer that comprises a sintered body 6 according to the invention. Like the porous sintered body 2 of FIG. 1 and FIG. 2, it is immersed in the liquid 1 to be vaporized. Due to capillary forces (represented by arrows 4), the liquid to be vaporized is conveyed into the entire volume of the sintered body 6. Sintered body 6 has an electrically conductive coating, the electrically conductive coating being provided on the surface defined by the open pores. Therefore, when a voltage is applied, the sintered body 6 is heated in the entire volume which has a large surface area. So, unlike in the vaporizer shown in FIG. 2, the liquid 1 is not only vaporized at the lateral surfaces of the sintered body, i.e. in a localized portion of the sintered body 6, but in the entire volume of the sintered body 6. Capillary transport to the lateral surfaces or heated surfaces or elements of the sintered body 6 is therefore not necessary. Moreover, there is no risk of local overheating. Since vaporization throughout the volume is much more efficient than when using a heating coil in a localized heated area, vaporization can occur at much lower temperatures and at lower heating power. Lower electrical power requirement is advantageous as it increases the life-cycle per battery charge or allows to install smaller rechargeable or disposable batteries.

Figure 4:
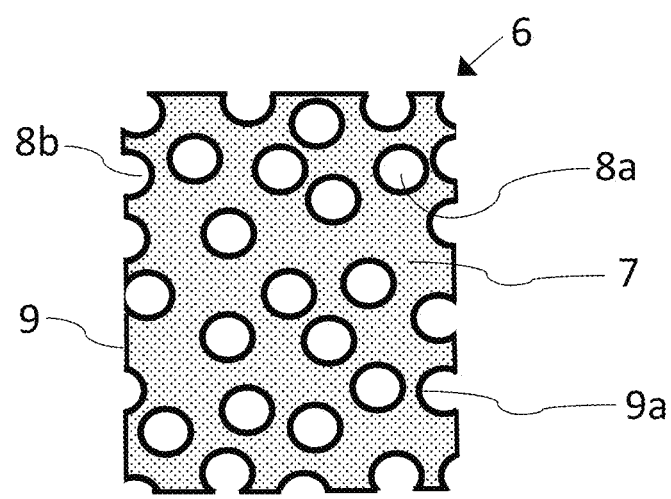
FIG. 4 is a schematic cross-sectional view of a sintered body coated according to the invention.

FIG. 4 shows the structure of a coated sintered body 6 with open porosity by way of a schematic cross-sectional view through one exemplary embodiment. The coated sintered body 6 comprises a porous sintered glass matrix 7 with open pores 8a, 8b. Part of the open pores 8b define, with their pore surface area, the lateral surfaces of the sintered body, while another part of the pores 8a define the interior of the sintered body. All of the pores of the sintered body are provided with an electrically conductive coating 9.

Figure 5:
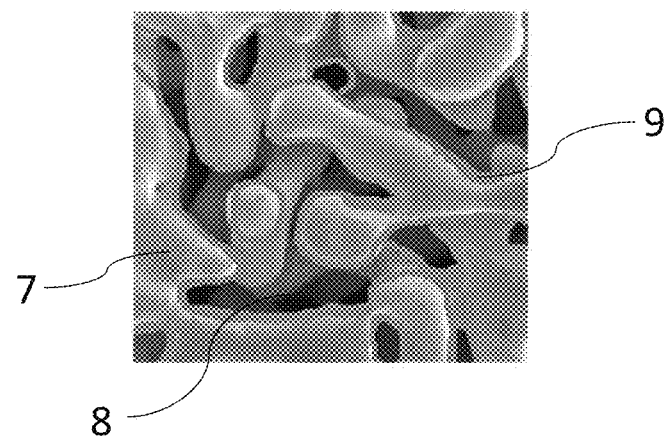
FIG. 5 shows an SEM image of a first exemplary embodiment.

FIG. 5 is an SEM micrograph of a sintered body with an electrically conductive coating. The surface of pores 8 is coated with an ITO layer 9 as an electrically conductive coating. The sintered glass matrix 7 is an aluminoborosilicate glass of the following composition:

Alkali oxides 1 to 11 wt %
Alkaline earth oxides 1 to 13 wt %
$B_2O_3$ 1 to 20 wt %
$Al_2O_3$ 1 to 17 wt %
$SiO_2$ 50 to 96 wt %.

A glass with the above composition melts very slowly and in a wide temperature range. Therefore, it is particularly suitable for producing porous materials by melting and sintering processes. Glasses of this composition range may have melting temperatures of more than 1000° C., which allows firing of the electrically conductive coating at temperatures of up to 900° C. and which has a positive effect on coating properties such as density and prevents cracks in the coating. The low coefficient of linear thermal expansion ($\alpha_{20\text{-}300° C.}$) of glass reduces thermally induced stresses and therefore increases the mechanical resilience of the material to temperature differences that occur in the vaporizer when being turned on and off. Furthermore, the glass with the electrically conductive coating as a heating element permanently resists temperatures of up to 600° C.

Figure 6:
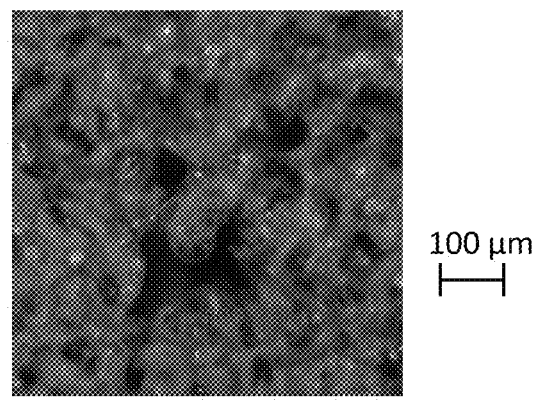
FIG. 6 is a photomicrograph of a second exemplary embodiment.

FIG. 6 shows a photomicrograph of a sintered body coated with an ITO layer.

Optical and electron microscopic measurements on the illustrated sintered body showed that the ITO layer has a thickness between 200 nm and 2000 nm and, surprisingly, does not exhibit any cracks. This is surprising, since the glass ($3.3*10^{-6}$ $K^{-1}$) and ITO ($7.2*10^{-6}$ $K^{-1}$) have different coefficients of linear thermal expansion.

Figure 7:
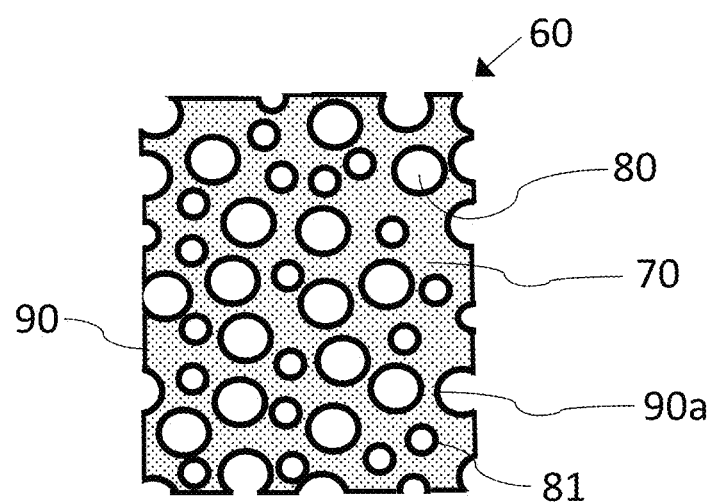
FIG. 7 is a schematic view of a refinement of the invention with a bimodal pore size distribution.

FIG. 7 is a schematic cross-sectional view illustrating the structure of a coated sintered body 60 according to one refinement of the invention. The coated sintered body 60 comprises a porous sintered glass matrix 70 with open pores 80, 81, the pores exhibiting a bimodal pore size distribution including large pores 80 and small pores 81. Part of the open pores define, with their pore surface area, the lateral surfaces of the sintered body, while another part of the pores define the interior of the sintered body. All of the pores of the sintered body are provided with an electrically conductive coating 90. The small pores 81 provide for good and rapid uptake of the liquid to be vaporized in the sintered body, while the large pores 80 provide for quick release of the vapor. Depending on the application, the uptake behavior and desorption properties during operation of the vaporizer can be adjusted through the ratio of large to small pores and the pore size.

Figure 8:
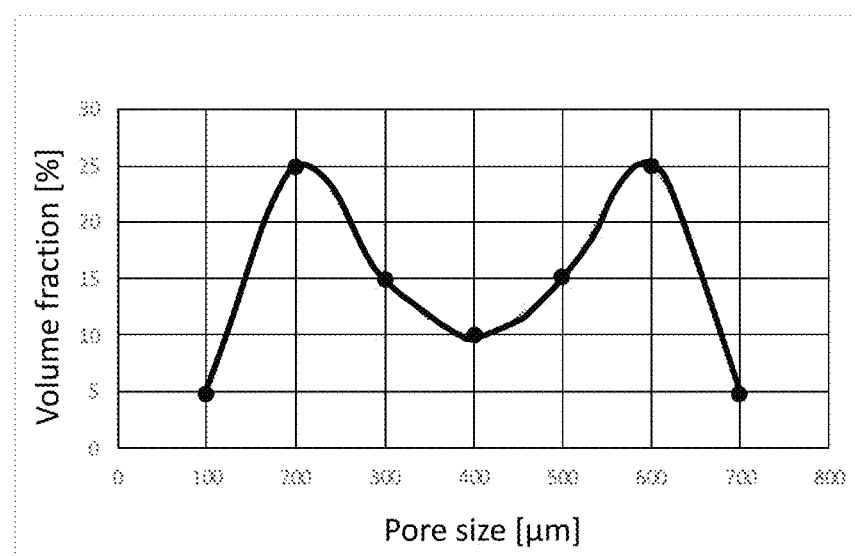
FIG. 8 illustrates the pore size distribution of a third exemplary embodiment.

FIG. 8 shows the pore size distribution of an exemplary embodiment of the refinement schematically illustrated in FIG. 7. Here, the pore size distribution of the porous sintered body has a maximum at about 200 µm and a maximum at about 600 µm, and the proportion of small pores (200 µm) corresponds to the proportion of large pores (600 µm) in this exemplary embodiment. The pore size can be adjusted during the manufacturing process through the grain size of the salt that is used as a pore former, and the ratio of large to small pores accordingly through the ratio of the grain sizes that are used and the grain size distributions thereof.

Figure 9A:
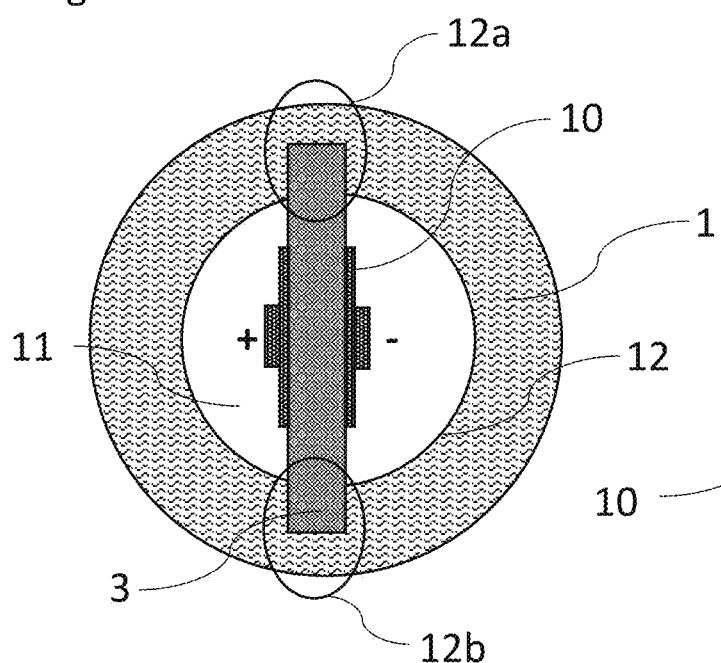
FIGS. 9a and 9b are schematic views of a sintered body coated according to the invention, as a component in a vaporizer.
Figure 9B:
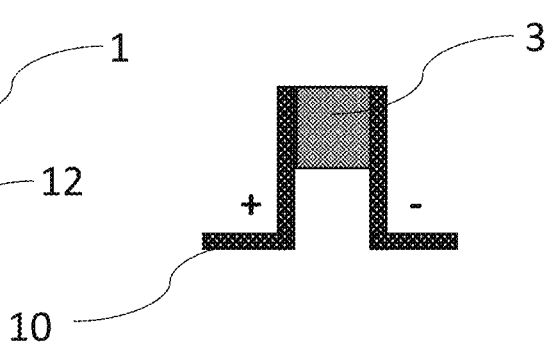

FIGS. 9a and 9b schematically show a sintered body 3 coated according to the invention as a component in a possible vaporizer. The vaporizer has a reservoir including the liquid 1 to be vaporized. The vaporization chamber 11 is separated from the liquid 1 to be vaporized by a steel wall 12. Through openings (12a, 12b) in the steel wall, the liquid 1 to be vaporized is in communication with the coated sintered body 3 which sucks in the liquid 1 to be vaporized by virtue of capillary forces. When a voltage 10 is applied to the sintered body 3 with the electrically conductive coating, the sintered body is heated throughout its volume, so that the liquid 1 is vaporized in the entire volume of the sintered body 3. Vaporization continues until the pores of the sintered body 3 and/or the reservoir no longer contain liquid 1 or the current flow is switched off. When the vaporizer is switched off, the pores will again suck in liquid, due to the capillary force, so that when the user turns on the vaporizer again, enough liquid 1 will again be available for vaporization.

The maximum possible amount of vapor that can be produced is equal to the amount of liquid that is or can be stored in the porous sintered body 3. The producible amount of vapor may therefore be controlled, for example, via the dimensions of the sintered body 3 and its porosity. Small sintered bodies with high porosity have proved to be particularly advantageous here in terms of efficiency of the vaporization process and of energy consumption and resupply of liquid or filling rate.

Figure 10A:
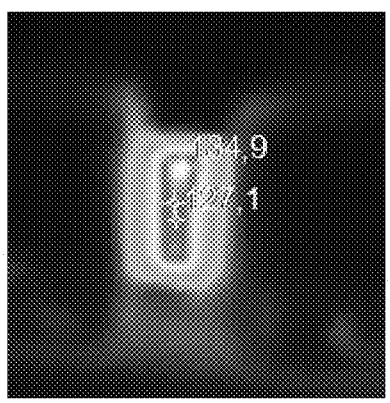
FIG. 10a shows a thermal image of a vaporizer with a sintered body coated according to the invention as a heating element.
Figure 10B:
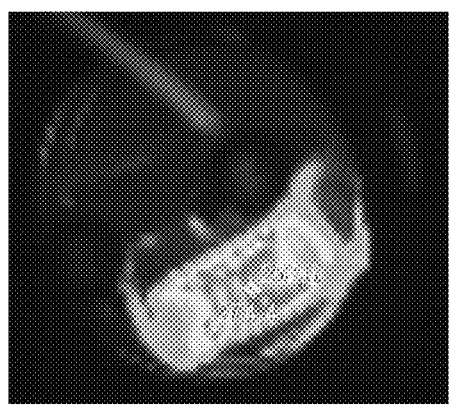
FIG. 10b shows a thermal image of a conventional vaporizer.

FIG. 10a shows a vaporizer comprising a sintered body coated according to the invention as a heating element and FIG. 10b shows thermal images of a conventional vaporizer and. While in the vaporizer with a sintered body coated according to the invention as a heating element of FIG. 10a, vaporization temperatures range from 127 to 135° C. only, a conventional vaporizer with a heating element in the form of a spiral heating wire of FIG. 10b requires vaporization temperatures in a range from 252 to 274° C. to produce the same or at least similar amount of vapor.

Table 3 shows vaporization parameters of a conventional vaporizer and of a vaporizer comprising a sintered body coated according to the invention as an exemplary embodiment. The respective vaporizers were operated in a configuration similar to an electronic cigarette. The output power was determined by measurement of the applied voltage and current flow using electrical measuring devices, the amount of generated vapor was determined through the weight loss of the liquid.

TABLE 3

COMPARISON OF VAPORIZERS

|  | Conventional vaporizer | Exemplary embodiment |
|---|---|---|
| Dimensions | OD = 5 mm, ID = 3 mm, length 12 mm | Hollow cylinder with OD = 6 mm, ID = 2 mm, length of cylinder 5 mm |
| Applied voltage | 4 V | 4 V |
| Heating power required | 16 W | 2 W |
| Operation temperature | 252-274° C. | 127-135° C. |
| Amount of vapor [milligram/min] | max. 72 | min. 72 |

As can be seen from Table 3, both vaporizers have a comparable size. In order to produce the same amount of vapor as a conventional vaporizer, a vaporizer with a sintered body coated according to the invention requires much lower heating power and lower vaporization temperatures.

For the exemplary embodiment, the vaporization temperature is significantly below the decomposition temperatures of the vaporizable substances that are typically used, so that so-called "coking" of the vaporizer by decomposition products will not occur and, therefore, a release of corresponding decomposition products is not to be expected. This increases the service life of the vaporizer.

Because of the lower heating power that is required, the vaporizer comprising a sintered body coated according to the invention is moreover far superior to a conventional vaporizer in terms of energy efficiency and the service life of the electrical power source.

What is claimed is:

1. A vaporizer comprising:
   a sintered body made of glass or glass ceramic and having open pores defining an open porosity in a range from 10 to 90%; and
   an electrically conductive coating that form part of a heating device of the vaporizer, wherein the electrically conductive coating is deposited on a surface of the sintered body and is bonded to the surface of the sintered body so that the electrically conductive coating lines the open pores located in an interior volume of the sintered body so that when the sintered body is connected electrically and an electrical current is applied the current flows at least partially through the interior volume of the sintered body heating the interior volume of the sintered body.

2. The vaporizer as in claim 1, wherein the open porosity is in a range from 50 to 80%.

3. The vaporizer as in claim 1, wherein the open pores have a pore size in a range from 1 μm to 5000 μm.

4. The vaporizer as in claim 1, wherein the sintered body further comprises closed pores, the sintered body having a proportion the closed pores in the total volume of the open pores of not more than 10%.

5. The vaporizer as in claim 1, wherein the open pores exhibit an at least bimodal pore size distribution.

6. The vaporizer as in claim 5, wherein the sintered body has large open pores with a pore size in a range from 500 to 700 μm and small open pores with a pore size in a range from 100 to 300 μm.

7. The vaporizer as in claim 6, further comprising a proportion of the large pores of 5 to 95%.

8. The vaporizer as in claim 1, wherein the sintered body is made of glass.

9. The vaporizer as in claim 8, wherein the glass has an alkali content of not more than 11 wt %.

10. The vaporizer as in claim 8, wherein the glass has a transition temperature $T_g$ in a range from 300 to 900° C.

11. The vaporizer as in claim 8, wherein the glass is an aluminoborosilicate glass containing the following constituents:
   $SiO_2$ 50 to 85 wt %
   $B_2O_3$ 1 to 20 wt %
   $Al_2O_3$ 1 to 17 wt %
   $\Sigma N_2O+K_2O$ 1 to 11 wt %
   $\Sigma MgO+CaO+BaO+SrO$ 1 to 13 wt %.

12. The vaporizer as in claim 8, wherein the sintered body has a coefficient of linear thermal expansion $\alpha_{20\text{-}300° C.\_sintered\ body}$ of not more than $20*10^{-6}$ $K^{-1}$ and wherein the electrically conductive coating has a coefficient of linear thermal expansion $\alpha_{20\text{-}300° C.\_coating}$ in a range from $1*10^{-6}$ $K^{-1}$ to $20*10^{-6} K^{-1}$.

13. The vaporizer as in claim 8, wherein the sintered body and the electrically conductive coating have a difference of coefficients of thermal expansion of $\Delta\alpha_{20\text{-}300° C.}=\alpha_{20\text{-}300° C.\_coating}-\alpha_{20\text{-}300° C.\_sintered\ body}$ from 0 to $20*10^{-6}K^{-1}$.

14. The vaporizer as in claim 1, wherein the sintered body provided with the electrically conductive coating exhibits an electrical conductivity in a range from 0.001 to $10^6$ S/m.

15. The vaporizer as in claim 1, wherein the electrically conductive coating comprises a metal oxide selected from the group consisting of indium tin oxide (ITO), aluminum-doped zinc oxide (AZO), fluorine tin oxide (FTO), antimony tin oxide (ATO), and combinations thereof.

16. The vaporizer as in claim 1, wherein the electrically conductive coating is made of a metal selected from the group consisting of silver, gold, platinum, chromium, and combinations thereof.

17. The vaporizer as in claim 1, wherein the electrically conductive coating has a thickness from 1 nm to 1000 μm.

18. The vaporizer as in claim 1, wherein the vaporizer configured for use as a component of an electronic cigarette or a medical inhaler or a fragrance dispenser or a room humidifier.

19. The vaporizer as in claim 1, wherein the sintered body with the electrically conductive coating applied thereon exhibits an electrical resistance in a range from 0.2 to 5 ohms, and wherein the vaporizer is operated at a voltage in a range from 1 to 12 V and/or at a heating power from 1 to 80 W.

20. The vaporizer as in claim 1, wherein the sintered body with the electrically conductive coating applied thereon exhibits an electrical resistance in a range from 0.2 ohms to 3000 ohms, and wherein the vaporizer is operated at a voltage in a range from 110 to 380 V and/or at a heating power from 10 to 1000 W.

21. The vaporizer as in claim 1, wherein the vaporizer is electrically connected through a mechanical connection or is electrically connected through an electrically conductive connector, or is electrically connected through an electrically conductive material bond.

22. The vaporizer as in claim 1, wherein the electrically conductive coating comprises at least one further component selected from the group consisting of an antimicrobial component, antibacterial component, silver, ZnO, $TiO_2$, and combinations thereof.

23. A vaporizer head, comprising:
a housing;
the vaporizer as in claim 1 in the housing, and
electrical contacts for connection of the sintered body.

24. A vaporizer comprising:
a sintered body made of glass or glass ceramic and having an outer surface, a volume, and open pores, the open pores defining an open porosity in a range from 10 to 90% of the volume; and
an electrically conductive coating lining at least some of the open pores throughout the volume of the sintered body so that, when a voltage is applied to the electrically conductive coating, a current will flow through the volume to heat the sintered body throughout the volume.

25. The vaporizer as in claim 24, wherein the open porosity is in a range from 50 to 80 and/or wherein the open pores have a pore size in a range from 1 μm to 5000 μm and/or wherein the open pores exhibit an at least bimodal pore size distribution.

26. The vaporizer as in claim 24, wherein the sintered body further comprises closed pores of not more than 10% of the volume.

27. The vaporizer as in claim 24, wherein the sintered body is made of glass having an alkali content of not more than 11 wt %.

28. The vaporizer as in claim 27, wherein the glass has a transition temperature $T_g$ in a range from 300 to 900° C.

29. The vaporizer as in claim 27, wherein the glass is an aluminoborosilicate glass containing the following constituents:
$SiO_2$ 50 to 85 wt %
$B_2O_3$ 1 to 20 wt %
$Al_2O_3$ 1 to 17 wt %
$\Sigma Na_2O+K_2O$ 1 to 11 wt %
$\Sigma MgO+CaO+BaO+SrO$ 1 to 13 wt %.

30. The vaporizer as in claim 24, wherein the sintered body has a coefficient of linear thermal expansion $\alpha_{20\text{-}300°\ C.\_sintered\ body}$ of not more than $20*10^{-6}\ K^{-1}$ and wherein the electrically conductive coating has a coefficient of linear thermal expansion $\alpha_{20\text{-}300°\ C.\_coating}$ in a range from $1*10^{-6}\ K^{-1}$ to $20*10^{-6}\ K^{-1}$.

31. The vaporizer as in claim 24, wherein the sintered body and the electrically conductive coating have a difference of coefficients of thermal expansion of $\Delta\alpha_{20\text{-}300°\ C.}=\alpha_{20\text{-}300°\ C.\_coating}-\alpha_{20\text{-}300°\ C.\_sintered\ body}$ from 0 to $20*10^{-6}\ K^{-1}$.

32. The vaporizer as in claim 24, wherein the electrically conductive coating comprises a material selected from a group consisting of indium tin oxide (ITO), aluminum-doped zinc oxide (AZO), fluorine tin oxide (FTO), antimony tin oxide (ATO), silver, gold, platinum, chromium, an antimicrobial component, an antibacterial component, ZnO, $TiO_2$, and combinations thereof.

33. The vaporizer as in claim 24, wherein the sintered body with the electrically conductive coating exhibits an electrical resistance in a range from 0.2 ohms to 3000 ohms.

* * * * *